(12) United States Patent
Hermansson et al.

(10) Patent No.: US 7,531,035 B2
(45) Date of Patent: May 12, 2009

(54) RESORBABLE CERAMIC COMPOSITIONS

(75) Inventors: Leif Hermansson, Uppsala (SE); Håkan Engqvist, Knivsta (SE)

(73) Assignee: Doxa AB, Uppsala (SE)

( * ) Notice: Subject to any disclaimer, the term of this patent is extended or adjusted under 35 U.S.C. 154(b) by 345 days.

(21) Appl. No.: 11/222,821

(22) Filed: Sep. 12, 2005

(65) Prior Publication Data
US 2006/0078590 A1    Apr. 13, 2006

(30) Foreign Application Priority Data
Sep. 10, 2004  (SE) .................................... 0402196

(51) Int. Cl.
    *C04B 7/02* (2006.01)
(52) U.S. Cl. .................. 106/713; 106/711; 106/35; 106/724; 106/733; 106/735; 106/737; 106/690; 106/716; 424/426
(58) Field of Classification Search .............. 106/713, 106/711, 35, 724, 733, 735, 737, 690, 716; 424/426
See application file for complete search history.

(56) References Cited

U.S. PATENT DOCUMENTS

| | | | |
|---|---|---|---|
| 5,415,547 A * | 5/1995 | Torabinejad et al. ..... 433/228.1 |
| 6,387,173 B2 * | 5/2002 | Greenwood et al. .......... 106/728 |
| 2002/0045678 A1 * | 4/2002 | Lopez et al. ................. 523/116 |
| 2003/0144384 A1 * | 7/2003 | Chen et al. ...................... 524/2 |
| 2004/0043053 A1 | 3/2004 | Yu et al. |
| 2005/0096280 A1 * | 5/2005 | Chun et al. ................... 514/22 |
| 2006/0102049 A1 * | 5/2006 | Bergaya et al. ............... 106/35 |

FOREIGN PATENT DOCUMENTS

| | | | |
|---|---|---|---|
| DE | 19923956 | * | 11/2000 |
| FR | 2843748 | * | 2/2004 |
| WO | WO2004058194 | | 7/2004 |

OTHER PUBLICATIONS

Saidon et al, "Cells and tissue reactions to mineral trioxide aggreagte and Portland cement", Oral Surgery Medicine Pathology, Apr. 2003, pp. 483-489.*
Britannica online Encyclopedia, "Cement", http://www.britannica.com/eb/article-76645, 2008.*
Translation for DE 19923956.*
J. Saidon et al., "Cell and tissue reactions to mineral trioxide aggregate and Portland cement", Oral Surgery Medicine Pathology, Apr. 2003, pp. 483-489.
S.M. Kenny and M. Buggy, "Bone cements and fillers: A review", Journal of Materials Science: Materials in Medicine, vol. 14, 2003, pp. 923-938.

* cited by examiner

*Primary Examiner*—C. Melissa Koslow
(74) *Attorney, Agent, or Firm*—Young & Thompson

(57) ABSTRACT

Ceramic precursor compositions and chemically bonded ceramic (CBC) materials, especially Ca-based, and a composite biomaterial suitable for orthopaedic applications. The CBC-system includes a binding phase (chemical cement) and additional phases with specified chemistry imparting to the biomaterial the ability of initial strength followed by interaction with the body tissue including body liquid, to form a resorbable or partly resorbable biomaterial. The ceramic precursor composition includes at least one silicate with Ca as the main cation with a resorption rate less or equal to that of the bone in-growth rate. The silicate will form the binding phase of the cured material. Implants and surface coated devices are also disclosed. The cured material exhibits a compressive strength exceeding 100 MPa.

25 Claims, No Drawings

RESORBABLE CERAMIC COMPOSITIONS

FIELD OF THE INVENTION

The present invention relates to ceramic precursor compositions and chemically bonded ceramic (CBC) materials, especially Ca-based, and a composite biomaterial suitable for orthopaedic applications. The CBC-system includes a binding phase (chemical cement) and additional phases with specified chemistry imparting to the biomaterial the ability of initial strength followed by interaction with the body tissue including body liquid, to form a resorbable or partly resorbable biomaterial. The invention also relates to a cured ceramic material, implants and surface coated devices.

BACKGROUND

For materials to be used as bone void fillers, which have to interact with human tissue, it is advantageous to make the biomaterials as biocompatible and bioactive as possible. This can be achieved principally by at least two routes—developing stable biocompatible materials or resorbable materials allowing new bone tissue to substitute the biomaterial. The first route to make more stable materials, e.g. PMMA-based materials or Ca-aluminate-based materials, is especially suitable for osteoporotic clinical situations. For active or young patients a resorbable material, e.g. soluble glasses and phosphate-based materials, may be the most attractive route, where interaction with living tissue is more pronounced. It is well known that calcium aluminates and calcium silicates can have a considerably higher compressive strength than those of the present resorbable materials (in the order of 100 MPa).

The traditional resorbable phases contain oxides of Ca and P (or S). Ca-phosphates and or Ca-sulphates and glass containing CaO, $P_2O_5$, $SiO_2$ and $Na_2O$ are typical representatives for this low-mechanical strength category of bioelements.

In EP 1 123 081 B1 and EP 0 555 807 Ca-silicate is mentioned as an additional phase for drug uses (less than 10%) and for bone substitute products as an additional divalent compound. Regarding biocompability of Ca-silicate materials, work have been done on the endodontic treatment material Proroot or MTA and on Wollastonite materials. See J. Saidon, et al, "Cells and tissue reactions to mineral trioxide aggregate and Portland cement", Oral surgery medicine pathology, April (2003) 483-489. Wollastonite is an established biomaterial in the form of sintered ceramic pieces. A survey of bone cements is found in S. M. Kenny and M. Buggy, "Bone cements and fillers: A Review", Journal of Materials Science: Materials in Medicine, 14 (2003) 923-938.

In view of the prior art materials for use, particularly in, bone void filling, there is a need for a biocompatible material exhibiting resorbability and sufficiently high strength, and thus load-bearing capacity, shortly after application, as well as later on.

BRIEF DESCRIPTION OF THE INVENTION

To fulfil the above-mentioned needs, the present invention provides ceramic precursor compositions and cured products exhibiting the above-mentioned features.

The object of the present invention is to provide ceramic precursor compositions based on chemically bonded ceramics as main phase(s), which when cured, provides a sufficiently high-strength (compressive strength 100-150 MPa) ceramic product. Said strength is achieved shortly after application of a slurry, paste or semi-hardened mixture of the ceramic precursor composition in a defective site. The initial high strength makes load-bearing possible for the defective site during the resorption stage, where new bone tissue takes over the load-bearing capacity.

During curing, the binding phase(s) according to the present invention consumes or takes up a great deal of water, whereby the cured ceramic product exhibits a low residual porosity, which contributes to the high strength.

According to a first aspect, there is provided a ceramic precursor composition comprising at least one particulate Ca-silicate, and possibly other particulate Ca-compounds selected from phosphates, carbonates, sulphates and combinations thereof, having calcium as the major cation. Said compound(s) will form the main binding phase(s) in the cured material.

In another embodiment, said ceramic precursor compositions also include a second binding phase (e.g. high-strength Ca-aluminates) contributing to the high compressive strength, both initially and later on.

The constituents of the ceramic precursor composition are particulate matter, unless stated otherwise. The percentages given for the precursor composition, as well as for the cured ceramic material, represent weight-%, unless stated otherwise.

According to second aspect, there is provided a cured ceramic material, which is obtained by mixing the precursor composition and a curing liquid, i.e. water.

According to third aspect, there is provided a medical implant which comprises the non-cured ceramic precursor composition and/or the cure ceramic material according to the invention. Said medical implant may be used as a carrier material for drug delivery. Therefore, the present invention also relates to such a carrier material for drug delivery.

According to fourth aspect, there is provided a surface coated device selected from the group consisting of an artificial orthopaedic device, a spinal implant, a joint implant, an attachment element, a bone nail, a bone screw, and a bone reinforcement plate, which device or substrate is coated with the non-cured ceramic precursor and/or the cured ceramic material according to the invention.

The major advantages of the present invention precursor composition, cured material and product, when inserted or injected into a body, is that they have a high resorbability, such that a high in-growth rate of a bone is achieved. The resorption rate is less or equal to that of the bone in-growth rate. This is important to keep the loading capacity during the whole healing period.

The compressive strength level obtained with the cured material according to the present invention is within the interval 100-150 MPa—to be compared with that of other resorbable biomaterials with a compressive strength in the interval 20-60 MPa.

The strength level for biomaterials according to the present invention is at least equal to that of stable biomaterials for bone void filler applications, such as PMMA-based materials, which do not exhibit the same degree of resorbability.

The ceramic material according to the invention have the advantages compared to prior art systems/materials, such as bioglasses, glass ionomer cements and pure Ca-phosphate-based systems or monomer-based filling materials, that it maintains its bioactivity, that it has improved initial strength and that it is dimensionally stable—i.e. exhibits a limited expansion instead of shrinking like known resorbable materials, which benefits the contact with the tissue.

The ceramic materials according to the invention have been especially developed for biomaterials used as bone void filler materials for orthopaedic applications, but can also be used as resorbable filler materials within odontology, including endodontics.

DETAILED DESCRIPTION OF THE INVENTION

The present invention deals with bioactive ceramics based on resorbable ceramics. However, in addition to this, the present invention also deals in detail with the time aspects of strength development and the level of strength obtained. Accordingly, the present invention aims at providing materials, preferably biomaterials, having early and maintained strength, which with time dissolves and interacts with the body system to yield new tissue.

In a basic form, the ceramic precursor composition according to the invention comprises main binding phase(s) of chemically bonded ceramics, preferably Ca-silicates, with Ca as the main cation. The binding phase(s) preferably comprises one or more of the following phases: $C3S=3(CaO)(SiO_2)$, $C2S=2(CaO)(SiO_2)$, and $CS=(CaO)(SiO_2)$. The main binding phase(s) of the ceramic precursor composition comprises more than 50 weight-% of at least one Ca-silicate. In a further preferred embodiment, the main binding phase comprises $3CaO \times SiO_2$. In a preferred embodiment, the main binding phase(s) of the cured ceramic material comprises hydrates of $3CaO \times SiO_2$. Said main binding phase(s) may also comprise phosphates, carbonates, sulphates of calcium, and combinations thereof. The remainder, if any, is constituted by additives such as inert phase and/or additives that make a material radiopaque.

The use of soluble chemically bonded ceramic based on $3CaO \times SiO_2$ is preferred, since it offers both resorbability, and a high initial consumption or up-take of water that reduces the porosity, whereby a high strength is achieved early after the application of the ceramic precursor composition mixed with a curing liquid.

As second binding phase(s), the ceramic precursor composition may further comprise a Ca-compound based on phosphate and/or sulphates in an amount of less than 20 weight-% of the main binding phase(s), preferably an amount of 5-10 weight-%. Said second binding phase may comprise a soluble glass, e.g. a phosphorous-containing glass, apatite-based materials, preferably a soluble CaH-phosphate.

The ceramic precursor composition may comprise additives conferring high radiopacity, e.g. sulphates such as Ba-sulphate, and other very slowly dissolving inorganic or inert mineral phases. Highly radio-opaque oxides, such as zirconium oxide, are preferred. These inert phases preferably comprises a Ca-silicate-based mineral or Ca-silicate glass. These glasses can preferably contain fluorine and phosphorus to yield fluoride and phosphate ions, which contribute to fluoroapatite formation. Said additives can be included in the composition in the form of glass particles, fibres, whiskers and/or platelets, in concentrations below 20 weight-% of the total composition, more preferably 5-15 weight-%, and most preferably 8-12 weight-%.

The ceramic precursor composition may further comprise particles of hydrated chemically bonded ceramics of the same or similar composition as that of the main binding phase(s) in an amount less than 40 weight-%, preferably 10-30 weight-%. This improves the homogeneity of the microstructure and enhances the binding between reacting chemically bonded ceramics and the filler material in the early stage of curing.

In order to further enhance early strength properties, additives may be included which improve initial closure of pores in the ceramic material by pure water up-take, e.g. from the semi-hydrate $CaSO_4 \times 1/2H_2O$ to gypsum ($CaSO_4 \times 2H_2O$). To solidify the total ceramic product initially, a combination of phosphoric acid and zinc oxide-forming Zn-phosphate is added. These phases will not contribute to the medium time or long-term properties, only enhance the initial pore closure and initial strength.

The initial strength up to a few hours after initialisation of the curing reaction may be further increased by addition of a polyacrylic (PA)-based material. When prior art glass ionomer cements (with PA-additives) are used as biomaterials, one major concern is the low pH and the low chemical stability of secondary phases. However, in the ceramic precursor compositions according to the present invention pure PA acid is used only in a low concentration, less than 8 weight-%, preferably less than 5 weight-% and more preferably 2-3 weight-%, and thus the acid works as an agent reducing the pH in early stages from a pH higher than 11-12 for the initially highly basic silicate and aluminate compounds, to a pH less than 10 within 60 minutes, preferably within 30 minutes in the mixture of the ceramic precursor composition and water.

In order to improve the long-term mechanical strength, high-strength stable additives based on other chemically bonded ceramics, preferably Ca-aluminates, forming hydrates in the cured material, are included in the ceramic precursor composition in an amount less than 40 weight-%, preferably 5-30 weight-%.

The viscosity of the ceramic material prior to curing can be controlled within a wide range, upon initial mixing of the powdered material and the hydration liquid, from moist granules to an injectable slurry. However it is preferable to decrease the water-to-cement (w/c) ratio as much as possible in order to obtain the appropriate viscosity for any given application. The w/c ratio should be less than 0.55, more preferably within the interval of 0.35-0.45. For orthopaedic applications the use of a somewhat higher w/c ratio than that of dental filling materials is possible and desirable to ensure an easily injectable biomaterial.

The materials also show slow disintegration rate in water and body liquid when inserted into a body, i.e. that >95% of the inserted mass is intact after a setting time of 5 minutes, more preferably after a setting time of 10 minutes. This is beneficial since it is important to allow the material to have time for setting without being too much mixed with the surrounding liquid. The setting time is in the interval of 5-12 minutes. The time for defined partial and complete disintegration can be varied within the interval of some months up to a few years.

The cured ceramic material exhibits a compressive strength exceeding 100 MPa. It has a compressive strength within 24 hours of at least 40 MPa, preferably more than 50 MPa within 1 h and more than 90 MPa within 24 h. The compressive strength exceeds 120 MPa after more than 7 days.

After more than 7 days after curing, the cured ceramic material exhibits a $K_{1c}$-value exceeding 0.5 $MPam^{1/2}$, preferably exceeding 0.7 $MPam^{1/2}$, and more preferably exceeding 1.0 $MPam^{1/2}$.

The dimensional change of the material during curing is less than 0.3 linear %, and/or exhibits an expansion pressure of less than 5 MPa, preferably less than 3 MPa.

The cured ceramic product according to the present invention, when inserted into a body, has a resorption rate that is less or equal to that of the bone in-growth rate. More than 60 weight-% of the material is dissolved within 3 years, preferably more than 50 weight-% within 2 years, and more preferably more than 40 weight-% within 12 months.

The term "bioelement" as used herein, means all types of ceramic or coated objects intended for insertion into a body, such as medical implants including carrier material for drug delivery, and particularly orthopaedic implants. The ceramic precursor composition according to the invention, mixed with a curing liquid, may also be inserted as a slurry, paste or putty, which after curing, forms said biolement.

EXAMPLE

An animal model was used to study the resorption rate for bone cement formulations containing calcium silicate as main binding phase(s).

Description of Raw Materials

The raw materials used were: tricalciumsilicate(C3S), dicalciumsilicate(C2S), monocalciumsilicate (CS) (Nycominerals), mono-calcium aluminate (CA), calcium-sulphate-semi-hydrate (Merck), tricalciumphosphate (Merck), dicalciumphosphate (Merck), apatite (Merck) and Norian (Syntes Stratec). The C3S, C2S and CA powders were synthesised in-house.

Description of Materials

A number of different powder formulations, that were prepared from the raw materials as mentioned above, are presented in Table 1:1.

Description of Tests

The powder formulations were mixed with water and a hardening accelerator (30 wt. % $CaCl_2$) to a calciumsilicate/water ratio of 0.4 using a mixing machine (Rotomix 3MESPE) and plastic jars. Mixing the water and powder yielded an injectable paste. The pastes were evaluated with respect to pH change and strength development (measured as compressive strength) over time. The samples submitted to compressive strength testing were stored in simulated body fluid (changed every third day) and subsequently measured after 1 h, 24 h, 7 days, 30 days, 3 months and 12 months. The samples submitted to pH testing were stored in simulated body liquid for 5 minutes, 30 minutes, 24 h, 7 days and 30 days. To some of the formulations (Formulations 1-2, 5-6 and 10-11) 2 wt-% of PA-acid was added. The pH change over time was detected.

Each paste was also inserted into an animal model. Bilateral defects were created in the distal femur of skeletally-mature female goats. The medial femoral condyle was exposed and a 10 mm diameter transverse defect was created from the medial cortex to the lateral cortical wall. The graft was placed in this defect site. Each formulation was tested in six sites. The animals were sacrificed after 52 weeks. The medial condyle was submitted to undecalcified histology. The samples were dehydrated, embedded in methyl methacrylate, sectioned in the coronal plane and ground to 20 micrometer thickness. Histomorphometry was conducted to measure bone-to-defect area, graft-to-defect ratio, and bone-to-graft ratio.

Results

The results from the strength test and the results from the resorption study is presented in the Tables 1:2 and 1:3. In the strength test, a commercial calcium phosphate cement was also tested (Norian) as a comparative ceramic. The pH shifted quickly from the initial interval of 11-12 for all formulations according to the invention to less than 10 after 30 minutes and less than 9 after 1 h. For samples including the addition of PA-acid, the pH change towards neutral was even quicker. The steady-state pH was higher than neutral.

TABLE 1:1

Composition of the tested formulations in vol. %.

| Formulation number | Tricalcium silicate | Dicalcium silicate | Mono calcium silicate | Mono calcium aluminate | Calcium sulphate | Tricalcium phosphate | Dicalcium phosphate | Apatite |
|---|---|---|---|---|---|---|---|---|
| 1 | 100 | | | | | | | |
| 2 | | 100 | | | | | | |
| 3 | 70 | | 15 | | 15 | | | |
| 4 | 70 | | | | 15 | 15 | | |
| 5 | 70 | | | | | | | 30 |
| 6 | 70 | | | | | | 30 | |
| 7 | 70 | | | | | 30 | | |
| 8 | 70 | | | 30 | | | | |
| 9 | 60 | 20 | | | | 20 | | |
| 10 | 60 | | | 20 | 20 | | | |
| 11 | 75 | | | 25 | | | | |
| 12 | 80 (20% hydrated) | | | 20 | | | | |

TABLE 1:2

The compressive strength development over time for the tested formulations (MPa).

| Formulation number | 1 h | 24 h | 7 days | 30 days | 3 months | 12 months |
|---|---|---|---|---|---|---|
| 1 | 60 | 100 | 150 | 150 | 150 | 150 |
| 2 | 40 | 85 | 110 | 130 | 130 | 130 |
| 3 | 50 | 100 | 110 | 110 | 90 | 90 |
| 4 | 50 | 90 | 100 | 110 | 80 | 80 |
| 5 | 45 | 90 | 90 | 120 | 120 | 120 |
| 6 | 50 | 95 | 100 | 125 | 125 | 125 |
| 7 | 55 | 100 | 120 | 125 | 130 | 130 |
| 8 | 40 | 70 | 90 | 100 | 90 | 70 |
| 9 | 55 | 100 | 110 | 130 | 130 | 130 |
| 10 | 60 | 100 | 120 | 130 | 130 | 130 |
| 11 | 70 | 105 | 130 | 130 | 130 | 130 |
| 12 | 60 | 100 | 130 | 130 | 130 | 130 |
| Norian (comparative) | 20 | 40 | 40 | 40 | 40 | 40 |

TABLE 1:3

Percentage of bone and graft material in defect site after 12 months

| Formulation number | % Bone | % Graft |
|---|---|---|
| 1 | 30 | 50 |
| 2 | 20 | 66 |
| 3 | 40 | 40 |
| 4 | 40 | 35 |
| 5 | 20 | 55 |
| 6 | 30 | 35 |
| 7 | 35 | 35 |
| 8 | 50 | 35 |
| 9 | 30 | 40 |
| 10 | 40 | 50 |
| 11 | 35 | 63 |
| 12 | 30 | 60 |

The results show that all formulations resorb over time and that the maximum strength but slowest resorption rate is achieved when using only calcium silicate as bone graft material.

The invention claimed is:

1. A ceramic precursor composition used for manufacturing resorbable or partly resorbable high-strength bloelements, comprising:
   at least one silicate with Ca as the main cation with a resorption rare loss or equal to that of bone in-growth rate, the at least one silicate being the main binding phase in a cured material;
   at least one second binding phase based on phosphates and/or sulphates in an amount of less than 20 weight-% of the main binding phase, the at least one second binding phase comprising a soluble glass; and
   optionally, additives selected from the group consisting of an inert phase, additives that make a cured material radiopaque, and mixtures thereof, wherein,
   the at least one Ca-silicate is present in an amount of greater than 50 weight-% of the ceramic precursor composition.

2. The ceramic precursor composition according to claim 1, wherein the main binding phase(s) further comprises phosphates, carbonates, sulphates of calcium, and combinations thereof.

3. The ceramic precursor composition according to claim 1, wherein the main binding phase(s) comprises $3CaO \times SiO_2$.

4. The ceramic precursor composition according to claim 1, wherein the soluble glass is a phosphorous-containing glass, apatite-based material.

5. The ceramic precursor composition according to claim 4, wherein the phosphorous-containing glass, apatite-based material is soluble CaH-phosphate.

6. The ceramic precursor composition according to claim 1, further comprising:
   additives selected from the group consisting of highly radio-opaque oxides and inorganic or inert mineral phases, wherein,
   the inorganic or inert mineral phases are selected from the group consisting of Ca-silicate-based mineral and Ca-silicate glass,
   and the additives are in a form of glass particles, fibres, whiskers and/or platelets.

7. The ceramic precursor composition according to claim 6, wherein said inorganic or inert mineral phases are present in an amount of less than 20 weight-%.

8. The ceramic precursor composition according to claim 1, further comprising hydrated particles of the main binding phase in an amount less than 40 weight-%.

9. The ceramic precursor composition according to claim 1, further comprising a ceramic powder of Ca-aluminate type in an amount less than 40 weight-%.

10. The ceramic precursor composition according to claim 1, further comprising less than 8 weight-% of a polyacrylic based material.

11. A cured chemically bonded ceramic material having a compressive strength exceeding 100 MPa for high-strength bioelements used as a resorbable or partly resorbable biomaterial, the cured cermic material comprising:
    a main binding phase comprising at least one silicate with Ca as a main cation with a resorption rate less or equal to that of bone in-growth rate;
    a least one second phase based on phosphates and/or sulphates in an amount of less than 20 weight-% of the main binding phase, the at least one phase comprising soluble glass; and
    optionally, additives selected from the group consisting of an inert phase, additives that make the material radiopaque, and mixtures thereof, wherein,
    the at least one Ca-silicate is present in an amount more than 50 weight-% of the cured ceramic material.

12. The cured ceramic material according to claim 11, wherein the main binding phase(s) further comprises components selected from the group consisting of phosphates, carbonates, sulphates of calcium, and combinations thereof.

13. The cured ceramic material according to claim 11, wherein the main binding phase(s) comprises hydrates of $3CaO \times SiO_2$.

14. The cured ceramic material according to claim 11, wherein the soluble glass is a phosphorous-containing glass, apatite-based material.

15. The cured ceramic material according to claim 14, wherein the phosphorous-containing glass, apatite-based materials soluble CaH-phosphate.

16. The cured ceramic material according to claim 11, further comprising inorganic or inert mineral phases of a Ca-silicate-based mineral or Ca-silicate glass.

17. The cured ceramic material according to claim 16, wherein the inorganic or inert mineral phases are present in an amount of less than 20 weight-%.

18. The cured ceramic material according to claim 11, further comprising a stable chemically bonded ceramic of Ca-aluminate hydrate type in an amount less than 40 weight-%.

19. The cured ceramic material according to claim 11, further comprising less than 8 weight-% of a polyacrylic-based material.

20. The cured ceramic material according to claim 11, wherein the material has a compressive strength within 24 hours of at least 40 MPa.

21. The cured ceramic material according to claim 11, wherein the material has a compressive strength exceeding 120 MPa after more than 7 days.

22. The cured ceramic material according to claim 11, wherein the material after more than 7 days after curing has a $K_{IC}$-value exceeding 0.5 $MPam^{1/2}$.

23. The cured ceramic material according to claim 11, wherein the material has a dimensional change of less than 0.3 linear %, and/or an expansion pressure during hardening and curing of less than 5 MPa.

24. The cured ceramic material according to claim 11, wherein the ceramic material, when inserted or injected into a body, has a disintegration rate in water and body liquid throughout the setting time such that >95% of the inserted mass is intact after a setting time of 5 minutes.

25. The cured ceramic material according to claim 11, wherein more than 60 weight-% of the material, when inserted in a body, is dissolved within 3 years.

* * * * *